United States Patent [19]
Cannon

[11] Patent Number: 6,045,623
[45] Date of Patent: Apr. 4, 2000

[54] METHOD AND APPARATUS FOR CLEANING CATHETER LUMENS

[76] Inventor: Bradley Jay Cannon, 110 S. Congress St., Newtown, Pa. 18940

[21] Appl. No.: 09/148,283

[22] Filed: Sep. 4, 1998

Related U.S. Application Data

[63] Continuation-in-part of application No. 08/845,825, Apr. 24, 1997, abandoned.

[51] Int. Cl.[7] ........................................................ B08B 9/00
[52] U.S. Cl. ........................... 134/8; 15/104.16; 15/104.2; 15/114; 15/206; 600/155; 604/267
[58] Field of Search ............................ 15/104.03, 104.05, 15/104.16, 104.165, 104.17–104.19, 104.2, 114, 164, 206, 211; 134/8; 422/28; 600/155; 604/267

[56] References Cited

U.S. PATENT DOCUMENTS

| | | | |
|---|---|---|---|
| 966,100 | 8/1910 | Johnson | 15/104.2 X |
| 2,303,660 | 12/1942 | Schickel | 15/206 X |
| 2,559,376 | 7/1951 | Schnitger | 15/104.2 X |
| 3,409,926 | 11/1968 | Martin | 15/114 |
| 5,297,310 | 3/1994 | Cox et al. | 15/104.2 X |
| 5,491,863 | 2/1996 | Dunn | 15/164 X |

FOREIGN PATENT DOCUMENTS 528464  5/1854  Belgium ................................ 15/114

*Primary Examiner*—Mark Spisich
*Attorney, Agent, or Firm*—William H. Meise

[57] ABSTRACT

A set (310) of lumen cleaning devices (310a, 310b, . . . ) is provided, with each consisting of a flexible shaft (312), a radial bristle brush (314) at one end of the shaft, and a swab (316) on the other end of the shaft. The brushes have particular brush diameters, may be stepped or tapered in diameter, and the swabs are dimensioned in conjunction with the maximum diameters of the brushes. The lumen of a medical device such as a catheter to be cleaned is first brushed with the brush end of a cleaning device selected to approximately match the lumen diameter. After brushing, the device is reversed, or preferably simply pushed through the lumen to be cleaned, and the swab end is used to remove any film remaining after the brushing. In a preferred method of cleaning, the brush end of the cleaning device is inserted into an end of the lumen to be cleaned, and pushed through only once, to avoid recontamination of the lumen by matter remaining on the brush. Cleansing or sterilizing solutions may be used in conjunction with the cleansing. The devices are color or otherwise coded to allow ready identification. In one embodiment, the brush and the swab are near one end of the shaft.

54 Claims, 8 Drawing Sheets

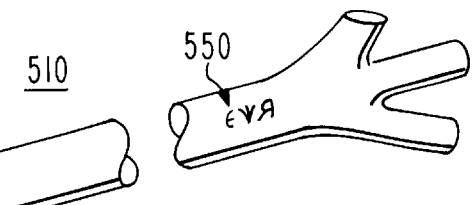
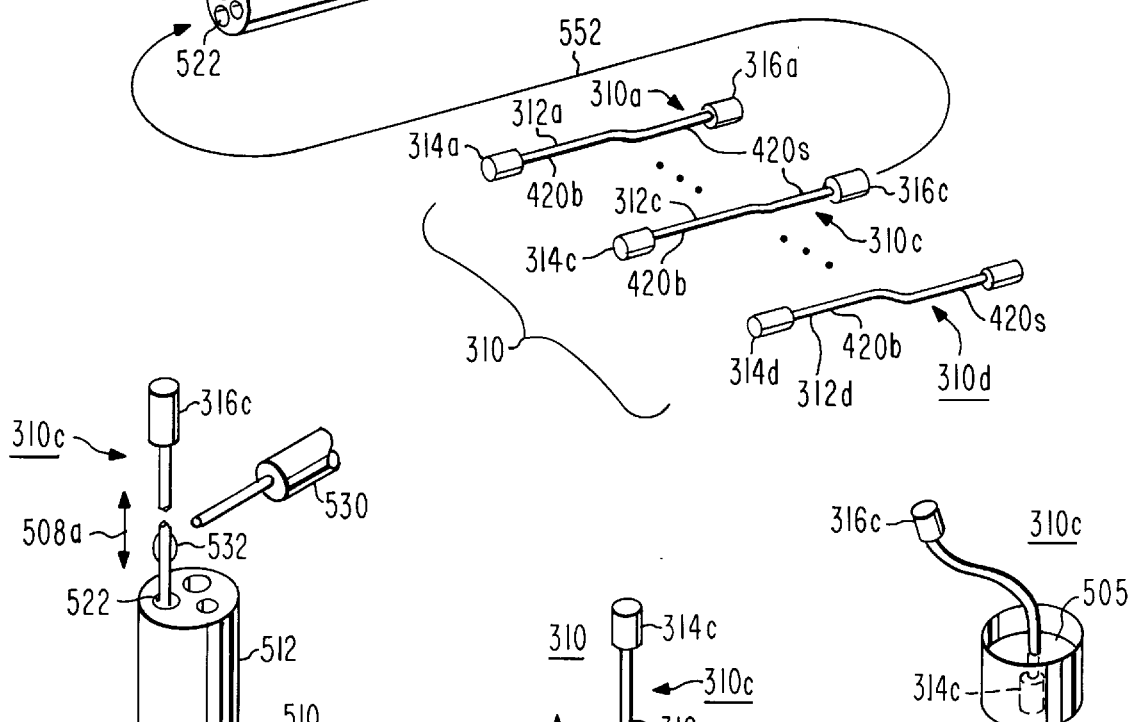
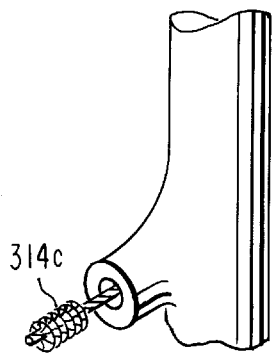
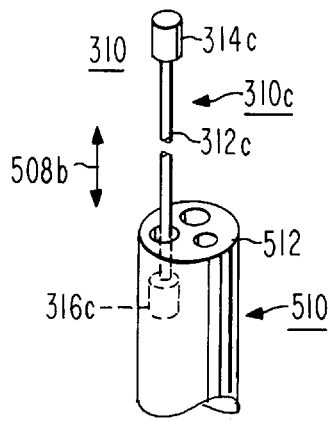
Fig.5a
Fig.5b
Fig.5c
Fig.5d

| Original | | | |
|---|---|---|---|
| Biopsy Channel | Suction Channel | Brush Range | Swab |
| 2.0mm | 3.7mm | 2.2mm | 2.2mm |
| 2.2mm | 3.7mm | 2.4mm | 2.4mm |
| 2.4mm | 3.7mm | 2.6mm | 2.6mm |
| 2.8mm | 3.7mm | 3.1mm | 3.1mm |
| 3.2mm | 3.7mm | 3.5mm | 3.5mm |
| 3.5mm | 3.7mm | 3.9mm | 3.9mm |
| 3.7mm | 3.7mm | 4.1mm | 4.1mm |
| 3.8mm | 3.7mm | 4.2mm | 4.2mm |
| 4.2mm | 3.7mm | 4.6mm | 4.6mm |
| Tapered | | | |
| 2.0mm | 3.7mm | 2.2 - 4.1mm | 4.1mm |
| 2.2mm | 3.7mm | 2.2 - 4.1mm | 4.1mm |
| 2.4mm | 3.7mm | 2.2 - 4.1mm | 4.1mm |
| 2.8mm | 3.7mm | 3.1 - 4.1mm | 4.1mm |
| 3.2mm | 3.7mm | 3.1 - 4.1mm | 4.1mm |
| 3.5mm | 3.7mm | 3.1 - 4.1mm | 4.1mm |
| 3.7mm | 3.7mm | 4.1mm | 4.1mm |
| 3.8mm | 3.7mm | 4.1mm | 4.1mm |
| 4.2mm | 3.7mm | 4.1 - 4.6mm | 4.1mm |
| Stepped | | | |
| 2.0mm | 3.7mm | 2.2mm & 4.1mm | 4.1mm |
| 2.2mm | 3.7mm | 2.4mm & 4.1mm | 4.1mm |
| 2.4mm | 3.7mm | 2.6mm & 4.1mm | 4.1mm |
| 2.8mm | 3.7mm | 3.1mm & 4.1mm | 4.1mm |
| 3.2mm | 3.7mm | 3.5mm & 4.1mm | 4.1mm |
| 3.5mm | 3.7mm | 3.9mm & 4.1mm | 4.1mm |
| 3.7mm | 3.7mm | 4.1mm | 4.1mm |
| 3.8mm | 3.7mm | 4.1mm & 4.2mm | 4.2mm |
| 4.2mm | 3.7mm | 4.1mm & 4.6mm | 4.6mm |

FIGURE 12

METHOD AND APPARATUS FOR CLEANING CATHETER LUMENS

This application is a continuation-in-part of U.S. patent application No. 08/845,825, filed Apr. 24, 1997, abandoned.

FIELD OF THE INVENTION

This invention relates to the cleaning of lumens of catheters and endoscopes used for medical procedures, and more particularly to the mechanical removal of biological material from the lumen of a catheter after use.

BACKGROUND OF THE INVENTION

Catheters are widely used in medical procedures for bronchoscopy, colonoscopy, gastroscopy, cardiac procedures, and the like. Many of these catheters have lumens which are used for infusions, or for removing ablated material, and as a consequence are subject to the flow of biological materials therethrough. Some of the catheters are disposable, as, for example, in the case of catheters for balloon angioplasty, while others, such as catheters such as endoscopes which include optical viewing devices, may be too expensive to discard after each use. In the case of such non-disposable catheters, the problem of cleaning and sterilizing the instrument in readiness for the next use must be confronted.

With the increase in the number of infectious diseases which are resistant to antibiotics, or not amenable to treatment for other reasons, it is very important to assure cleanliness of reusable catheters. The procedures for cleaning the lumens of catheters is rendered difficult by the small diameters of the lumens, and their considerable lengths. Lumens for endoscopes, for example, may range in diameter from about 2.0 to about 3.2 millimeters (mm), or even 3.7 mm, and the length of a lumen may be as great as 110 centimeters (cm), corresponding to ratios of length-to-diameter of as much as about 35:1. In addition, the lumens may be curved, which exacerbates the cleaning problem.

Improved lumen cleaning arrangements are desired.

SUMMARY OF THE INVENTION

A method for cleaning a lumen of a medical device adapted for introduction into a vas of the body of a patient, where the lumen has a diameter lying in the range of about 2.0 to about 3.2 millimeters, includes the step of providing a set of endoscope lumen cleaning devices. The set of lumen cleaning devices includes a plurality of members, and each member of the set of the lumen cleaning devices includes a shaft, a brush, and a swab. The shaft is elongated and flexible, and defines a brush end and a second end. The shaft has a diameter which is less than about 1.8 mm, and preferably less than one and one-half millimeters and a length greater than about 110 centimeters. The brush is a bristle brush affixed to the shaft near the brush end of the lumen cleaning device, with the bristles of the brush being radially disposed relative to the shaft. The tips of the brush bristles define or provide a circumferential brushing surface defining or having a diameter. The swab surrounds the shaft near the second end of the lumen cleaning device in one embodiment, or in another embodiment at a location which is closer to the second end of the shaft than the location of the brush. The swab is made from a material which is elastically deformable. The bristles of the brush define one of a plurality of discrete brush diameters in each of the members of the set of lumen cleaning devices. The various members of the set have brush diameters which range in discrete steps from about 2.0 to about 3.2 millimeters. The swab of each of the members of the set of lumen cleaning devices has an outer diameter which is no less than the diameter of its corresponding brush. Thus, each member of the set of lumen cleaning devices includes a brush which is approximately matched to the diameter of the lumen to be cleaned, and a swab which has a diameter which is related to the diameter of its associated brush.

A mode of the inventive cleaning method includes the steps of selecting a cleaning device from the set, where the brush diameter of the selected one of the cleaning devices is the smallest one of the set which is larger than the diameter of the lumen to be cleaned. Thus, the brush will always be slightly larger than the lumen in which it is used, but only slightly larger. The lumen is brushed with the selected brush, and cleansing (including disinfectant) fluid may, if desired, be introduced in conjunction with the brushing. The brushing may remove most particulate matter from the lumen, but a film of matter may remain. Because of the length and small diameter of the lumen being cleaned, it may not be possible to see the remaining film. The brush end of the lumen cleaning device exits the lumen, and the swab is introduced, if not already in the lumen, and the lumen is swabbed. The swabbing may be in conjunction with cleansing fluid, if desired. The swabbing tends to remove the remaining film. The brush and the swab may be pushed or pulled completely through the lumen during this procedure.

The brushes may have diameters which increase in diameter in a linear manner from member to member of the set, as for example by having approximate diameters which include 2.0, 2.2, 2.4, . . . , 3.0, 3.2 millimeters, where the incremental diameter from member to member of the set is about 0.2 mm. Another increment scheme is that of a geometric increase in diameter, such as an approximate 10% increase in diameter from one member to another, which gives diameters including about 2.0, 2.2, 2.4, 2.7, 3.0, and 3.3. millimeters.

The brushing and swabbing may be accompanied by the use of liquid cleansing or disinfecting material, as by introducing the liquid into the lumen by submerging the endoscope in the liquid cleansing material, by pouring the material into the lumen during brushing or swabbing, or by dipping the brush or swab into the liquid before introduction into the lumen.

A set of lumen cleaning devices according to an aspect of the invention includes a plurality of members of the set. Each member of the set of lumen cleaning devices includes an elongated, flexible shaft having a diameter not exceeding 1.8 millimeters, and preferably no greater than one and one-half millimeters in diameter, and having a length of more than 110 centimeters. The shaft defines a brush end and a second end. A brush is affixed to the shaft near the brush end of the shaft. The brush includes a plurality of bristles affixed to the shaft, the tips of which, together, define a right circular cylindrical brushing surface generally centered on the shaft. The cylindrical brushing surface (or the diameter of the brush from tip to tip of the bristles) defines a diameter lying in the range of about 2.0 to about 3.2 millimeters. The diameter of the brush is different among the different members of the set of lumen cleaning devices. For example, a first member of the set of lumen cleaning devices might have a brush diameter of about 2.0 mm, another member of the set might have a brush diameter of about 2.2 mm, and so forth. A swab is affixed to, and surrounds, the shaft at a location closer to the second end of the shaft than the location of the brush. The swab is made from a deformable elastic material such as foam. The swab may be attached to the shaft by being molded about the shaft, whereby its structure fills the interstices in the shaft. The swab generally defines a right circular swabbing surface, which is generally centered on the shaft. The diameter of the swabbing surface of the swab is no less than the diameter of the brushing surface. A particular set of lumen cleaning devices has members of the set having brush diameters of about 2.0, 2.4, 2.8, and 3.2 millimeters. Another possible set has brush diameters of about 2.0, 2.2, 2.4, and 2.7 millimeters, and this set may further include brushes having diameters of about 3.0 and 3.2 mm.

In one manifestation of the invention, a cleaning device for a lumen of a catheter includes a flexible shaft having a diameter no greater than about two millimeters. The shaft defines a brush end and a second end. A generally cylindrical brush is affixed to the shaft near the brush end of the shaft. In this context, "near" includes "at" the brush end. The cylindrical brush has a diameter (that is, its bristle portion has a diameter) lying between about 3 and 4 millimeters, for some purposes closer to 5 mm than to 4 mm. The cleaning device includes an elastomeric, generally cylindrical swab affixed to the shaft at a location between the brush and the second end of the shaft. The swab has a diameter no smaller than the diameter of the brush.

In a further avatar of the invention, a cleaning device for a lumen of a catheter includes a flexible shaft having a diameter no greater than about two millimeters. The shaft defines a brush end and a second end. The cleaning device includes a plurality of generally cylindrical brushes affixed to the shaft near the brush end of the shaft. The cylindrical brushes having diameters lying between about 2 and 5 millimeters. The cleaning device further includes an elastomeric, generally cylindrical swab affixed to the shaft at a location which lies between the brush and the second end of the shaft. The location of the swab may be at the second end of the shaft. The swab has a maximum diameter no smaller than the diameter of that one of the plurality of brushes having the largest diameter. In this arrangement, the shaft defines an axis of elongation, and the brushes are separated from each other by "non-brush" regions or spaces lacking bristles, or lacking bristles of significant length. The space(s) have axial lengths related to the radii of those of the brushes which are immediately adjacent to the spaces. In a particularly advantageous incarnation of the invention, the bristles of the brushes are made from polymer, preferably nylon. A particular version of this avatar is one in which the number of brushes on each shaft is two, and the brushes have diameters of about 2.2 mm and 4.1 mm, and the swab has a diameter not less than 4.1 mm. Another hypostasis or version, also with two brushes, has brush diameters of about 2.4 mm and 4.1 mm, and the swab has a diameter not less than 4.1 mm. In other two-brush versions, the brushes have diameters of about 2.65 & 4.1 mm; 3.1 & 4.1 mm; 3.5 & 4.1 mm; 3.85 & 4.1 mm, and in all of these versions the swab has a diameter of not less than 4.1 mm. In another version, the number of brushes is two, and the brushes have diameters of about 4.1 mm and 4.6 mm; the swab has a diameter not less than 4.6 mm. In any of the above objectifications of the invention, the swab may be located closer to the brush end of the shaft than to the second end of the shaft. In a preferred embodiment, that one of the brushes having the smallest diameter among the brushes is closest to the brush end of the shaft. Where there are more than two brushes, the brushes preferably arrayed on the shaft in such a manner that those of the brushes having a particular diameter are more remote from the brush end of the shaft than all of the brushes having diameters less than the particular diameter Another particularly advantageous embodiment is one in which the swab includes a portion with a tapered diameter, and the smallest-diameter portion of the swab is closer to the brush end of the shaft than that portion of the swab having the maximum diameter. In this avatar, the preferred shaft includes a metallic inner portion or core, surrounded by a polymeric tube, which may be, for example, polyethylene.

A cleaning device for a lumen of a catheter according to yet a further avatar, embodiment, hypostasis, manifestation, objectification of the multifarious invention includes a flexible shaft having a diameter no greater than about two millimeters. The shaft defines a brush end and a second or other end. The cleaning device includes a plurality of generally cylindrical brushes affixed to the shaft near the brush end of the shaft. The cylindrical brushes have diameters lying between about 2 and 5 millimeters. The cleaning device further includes an elastomeric, generally cylindrical swab affixed to the shaft at a location which lies between the brushes and the second end of the shaft. The location of the swab may be at or near the second end of the shaft. The swab has a maximum diameter no smaller than the diameter of that one of the plurality of brushes having the largest diameter. In one version of this arrangement, the shaft defines an axis of elongation, and the brushes are separated from each other, in a direction parallel to the axis of elongation, by "non-brush" regions or space(s) lacking bristles. The space(s) have axial lengths related to the radii of those of the brushes which are immediately adjacent to the spaces. More particularly, the space(s) are selected in axial length, so that when the bristles of the larger of the two adjacent brushes are bent over toward the smaller of the adjacent brushes when the larger brush precedes the smaller brush through the lumen being cleaned, they do not overlap into the region occupied by the smaller brush. In a particularly advantageous embodiment of the invention, the bristles of the brushes are made from polymer, preferably nylon. A particular version of this avatar is one in which the number of brushes on each shaft is two, and the brushes have diameters of about 2.2 mm and 4.1 mm, and the swab has a diameter not less than 4.1 mm. Another version, also with two brushes, has brush diameters of about 2.4 mm and 4.1 mm, and the swab has a diameter not less than 4.1 mm. In other two-brush versions, the brushes have diameters of about 2.65 & 4.1 mm; 3.1 & 4.1 mm; 3.5 & 4.1 mm; 3.85 & 4.1 mm, and in all of these versions the swab has a diameter of not less than 4.1 mm. In another version, the number of brushes is two, and the brushes have diameters of about 4.1 mm and 4.6 mm; the swab has a diameter not less than 4.6 mm. In any of the above versions, the swab may be located closer to the brush end of the shaft than to the second end of the shaft. In a preferred embodiment, that one of the brushes having the smallest diameter among the brushes is closest to the brush end of the shaft. Where there are more than two brushes, the brushes preferably arrayed on the shaft in such a manner that those of the brushes having a particular diameter are more remote from the brush end of the shaft than all of the brushes having diameters less than the particular diameter. Another particularly advantageous embodiment is one in which the swab includes a portion with a tapered diameter, and the smallest-diameter portion of the swab is closer to the brush end of the shaft than that portion of the swab having the maximum diameter. In this avatar, the preferred shaft includes a metallic inner portion or core, surrounded by a polymeric tube, which may be, for example, polyethylene.

A cleaning device for a lumen of a catheter according to yet another embodiment of the invention includes a flexible shaft having a diameter no greater than about two millimeters. The shaft defines a brush end, a second end, and an axis of elongation. A brush, in the form of the frustum of a cone, is affixed to the shaft near the brush end of the shaft, with the axis of the frustum substantially coincident with the axis of elongation. The brush has a smallest diameter of about 2 millimeters, and a largest diameter less than about 5 millimeters. The cleaning device includes an elastomeric, generally cylindrical swab affixed to the shaft at a location between the brush and the second end of the shaft. The swab has a diameter no smaller than the largest diameter of the brush. For cleaning catheters having biopsy channel lumens in the range of about 2.0 to 2.4 mm in diameter and suction channel lumens in the range of about 3.7 mm, the tapered brush has a diameter ranging from about 2.2 to about 4.1 mm, and a swab diameter of about 4.1 mm. For cleaning catheters having biopsy channel lumens in the range of about 2.8 to 3.5 mm in diameter and suction channel lumens in the range of about 3.7 mm, the tapered brush has a diameter ranging from about 3.1 to about 4.1 mm, and a swab diameter of about 4.1 mm. For cleaning catheters having biopsy channel lumens with a diameter of about 4.2 mm and suction channel lumen in the range of about 3.7 mm, the tapered brush has a diameter ranging from about 4.1 to about 4.6 mm, and a swab diameter of about 4.6 mm. For cleaning catheters having biopsy channel lumens in the range of about 3.7 to 3.8 mm and suction channel lumens in the range of about 3.7 mm, the brush is not tapered, but has a diameter of about 4.1 mm, and a swab diameter which is also about 4.1 mm. The shafts of these embodiments are at least 100 cm long, and preferably greater than 110 cm.

A method according to a mode of the invention includes the steps of inserting the brush end of any of the above-described lumen cleaning devices into the lumen to be cleaned, and pushing the brush through the lumen until it protrudes from the opposite side of the lumen. The brush is grasped, and the entire cleaning device, including the swab, is pulled through the lumen.

BRIEF DESCRIPTION OF THE DRAWING

FIG. 4b illustrates a detail of the shaft of the member of FIG. 4a;

FIGS. 5a, 5b, 5c, 5d, and 5e represent particular steps in the cleaning of a lumen of a catheter in accordance with the invention, using a member of the set of FIG. 3;

FIG. 8b is a cross-sectional view which illustrates details of the construction of a lumen cleaning device of FIG. 8a;

FIG. 12 tabulates the preferred range of brush diameters and swab diameters for cleaning the biopsy channel and suction channel lumens (or of other lumens) of catheters, where the lumens of a particular catheter have the given dimensions of biopsy channel and suction channel.

DESCRIPTION OF THE INVENTION

Figure 1:
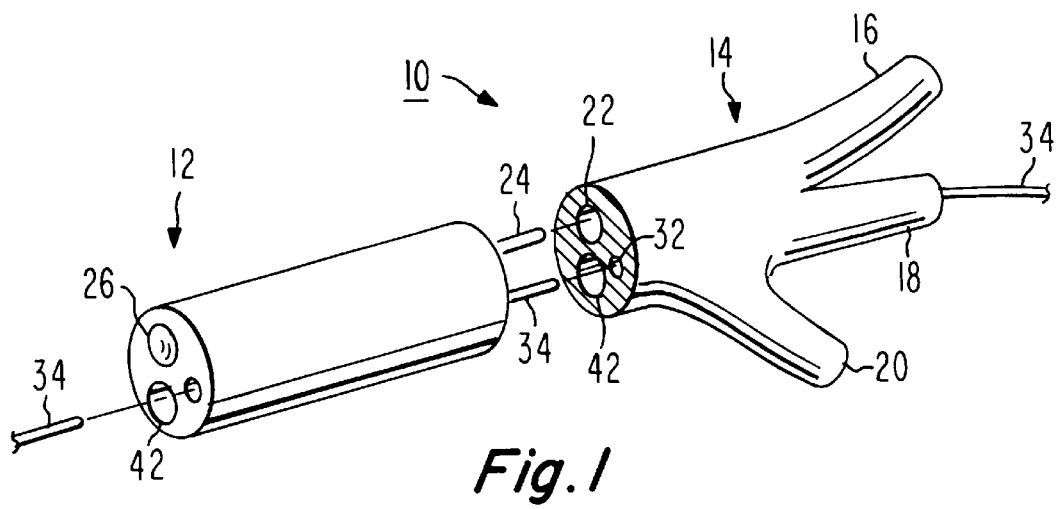
FIG. 1 is a simplified illustration of a catheter representative of the prior art, which includes a lumen which requires cleaning.

FIG. 1 is a simplified perspective or isometric representation, partially cut away to reveal interior details, of an elongated catheter 10 defining a distal end 12 and a proximal end 14, which is furcated or branched into branches 16, 18, and 20. A plurality of bores extend from distal end 12 to the various proximal branches 16, 18, and 20. More particularly, a first bore 22 is occupied by a fiber optic scope including an optical fiber arrangement illustrated as 24, which extends from an eyepiece coupled to proximal branch 16, to allow observation of those portions of the patient adjacent to distal end 12. The distal end of bore 22 is sealed against ingress of biological material by a lens arrangement 26. A second bore 32 extends from proximal branch 18 to the distal end 12 of the catheter 10, and is dimensioned to accommodate a guide wire, illustrated as 34. A third lumen 42 extends from distal end 12 of catheter 10, and exits at a port (not visible in FIG. 1) at the proximal end of proximal branch 20. Lumen 42 is used for infusion of medication or for removal of biological material from the patient, as might be the case when, for example, the catheter includes an ablation device (not illustrated) which dislodges material from the walls of the vas, and the material so dislodged should be removed from the body. When the catheter of FIG. 1 is used by insertion into a vas of a patient, bores 32 and 42 may, and probably will, become soiled with biological materials.

Since catheter 10 includes a fiber optic scope or other complex instrument, it may be too expensive to simply dispose of after a single use on a patient. If the catheter is to be reused, it must be thoroughly cleaned and sterilized before the next use. One common method for cleaning the lumens of such multi-use catheters is to use a cylindrical brush on the end of an elongated shaft, followed by use of a cleaning or sterilizing solution. The cleaning often consists of a single forward and return swipe through the lumen with a standard-size brush, which is to say with a general-purpose cleaning brush having a diameter unrelated to the exact size of the lumen being cleaned.

Figure 2:
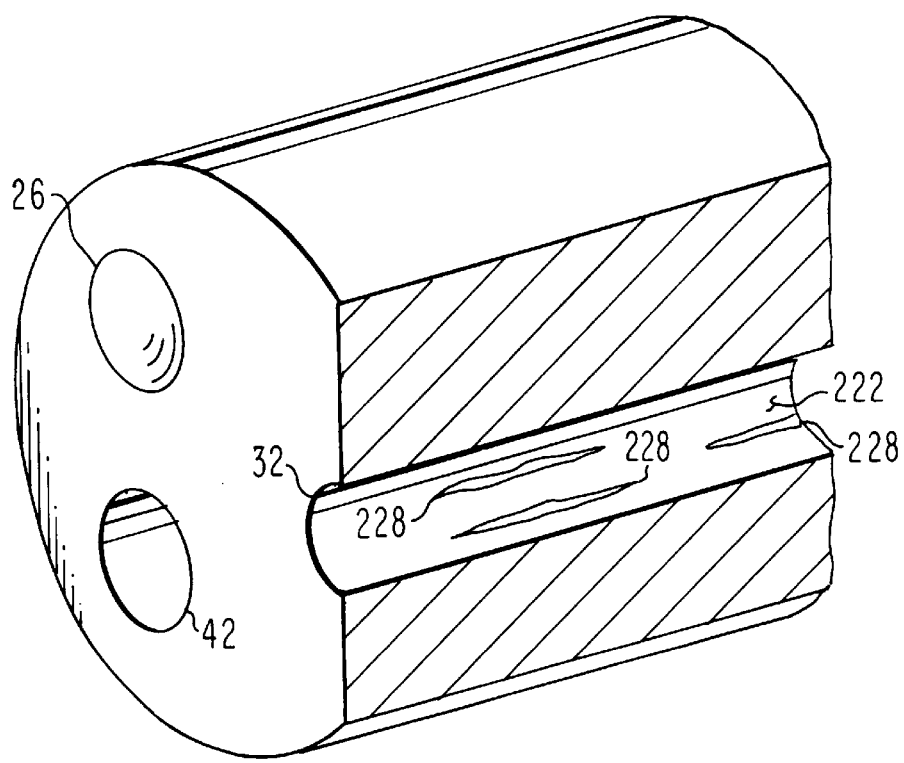
FIG. 2 is a representation of the interior of a portion of a lumen of the catheter of FIG. 1, split and opened to reveal the interior surface after cleaning by a brush, showing regions in which film remains.

FIG. 2 illustrates the distal end 12 of catheter 10, with lumen 22 split open, to reveal the inner surface after several swipes with a general-purpose cylindrical cleaning brush which is significantly oversize relative to the lumen diameter. In this context, the term "significantly" means that the brush diameter is such that the bristles are bent to the extent that the sides of the bristles, rather than their tips, are in contact with the sides or walls of the lumen. As illustrated in FIG. 2, the interior surface 222 of lumen 22 is mostly clean, as the brushing has removed all solid matter, but certain thin regions 228, elongated in the direction of elongation of the lumen, remain covered with a film of biological material. The film regions 228 may remain as a result of use of a brush which is not suitably dimensioned to the lumen, or too few passes of the brush through the lumen, or possibly for other reasons.

Figure 3:
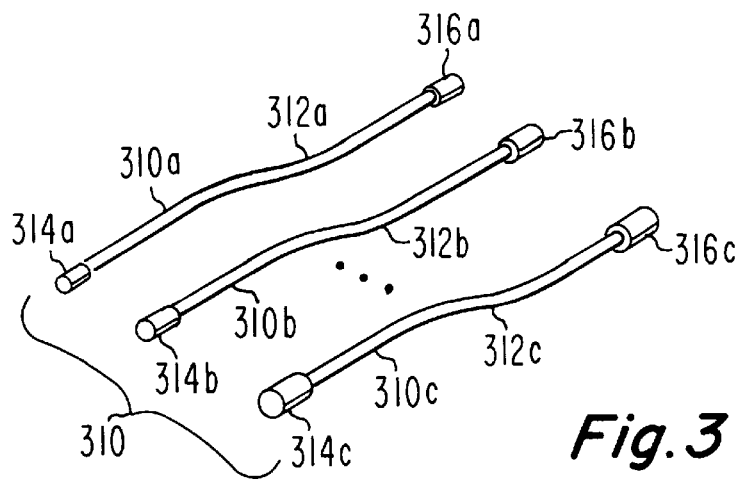
FIG. 3 is a simplified representation of a set of lumen cleaning devices in accordance with an aspect of the invention.

According to an aspect of the invention, a set of cleaning devices, such as the set 310 illustrated in FIG. 3, is provided for use in cleaning the lumens of catheters. In FIG. 3, set 310 includes a number of members, some of which are illustrated as 310a, 310b, and 310c. Each of these cleaning devices 310a, 310b, . . . , 310c includes a flexible shaft 312a, 312b, . . . , 312c, which is capable of traversing bends in the lumen, such as the bends which must occur in bore 42 as it makes the curve into proximal branch 20. Each shaft 312a, 312b, . . . , 312c must be small in enough in diameter to be flexible, but may not have a diameter equal to or greater than that of the smallest lumen. Thus, the shaft diameter may not exceed about 1.8 mm, but may be as much smaller as the rigidity of the structural material allows while allowing the brush to be pushed through the bore.

The shaft 312a, 312b, . . . , 312c of each member of the set 310 of cleaning devices of FIG. 3 has a brush 314a, 314b, . . . , 314c affixed thereto, which is dimensioned to more or less precisely fit a certain range of lumen bore diameters. The bore diameters of lumens of catheters of the sort requiring cleaning range from about 2.0 millimeters (mm) to about 3.2 mm, and their lengths may be in the range of about 110 cm to about 230 cm. To accommodate the length of the longest lumen, the shaft lengths of the cleaning devices of set 310 are uniform, and in the range of about 240 cm. The brushes 314a, 314b, 314c have approximately cylindrical brushing surfaces, the smallest of which has a diameter of about 2.0 mm, and the largest of which has a brush diameter of about 3.2 mm.

Since it is possible that the person cleaning the catheter may do so in a perfunctory manner, it may not be possible to guarantee that multiple swipes of the brush though the lumen will be made, especially if there are multiple lumens in the catheter which must be cleaned. Therefore, there is the possibility that areas of biological film will remain within the catheter lumen after it is brushed. Such remaining material is undesirable, because it may prevent fluid sterilizing material from coming into full contact with all regions having microbes, and thereby prevent full sterilization. Even if the film becomes sterile by sterilizing the catheter in an autoclave, the film may contain proteins or biological materials to which the next user of the catheter is allergic. According to a further aspect of the invention, each member 310a, 310b, . . . , 310c of the set of lumen cleaning devices of FIG. 3 also has a swab 316a, 316b, . . . , 316c mounted on the shaft at the second end of the shaft from the brush end, which in this embodiment may be termed a "swab" end. The swab consists of a material which can be deformed, but which is sufficiently elastic to bear against the walls of the lumen. The diameter of the swab is selected to be slightly larger than the brush diameter with which it is associated on the shaft, so that the swab is at least slightly compressed even with the largest lumen in which the brush can be used. This slight compression provides the radial force necessary for the swab to tend to wipe away regions of film.

Incidentally, it should be noted that a set such as set 310 of FIG. 3 remains a set even though it may have disparate numbers of each member; thus, even if there are two units of member 310a, together with the other members 310b, . . . , 310c, a set 310 still exists, and a set 310 still exists even if some members of the set are missing. This might occur, for example, if the manufacturer of the set 310 of cleaning devices makes all the members, and a dealer or user purchases for use or stock only selected ones of the set, such as only member 310b.

Figure 4A:
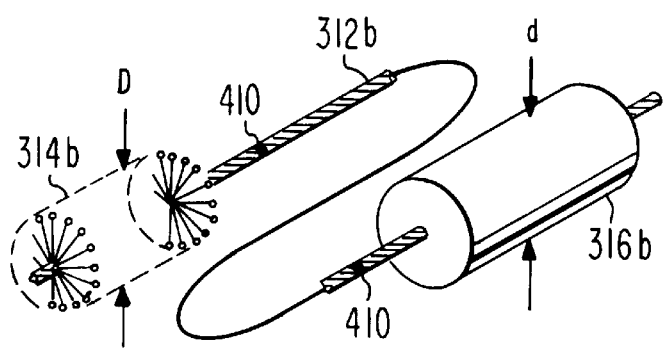
FIG. 4a is a more detailed view of a particular member of the set of FIG. 3.

FIG. 4a is a more detailed illustration of one member of set 310 of FIG. 3, taken as being representative of all of the members, except, of course, for the sizes of the brushes and associated swabs. For definiteness, member 310b of set 310 of lumen cleaning devices is illustrated in FIG. 4a. As illustrated in FIG. 4a, shaft 312b of member 310b is made up of two or more flexible metallic wires, twisted together to form a flexible shaft. At the brush end of the shaft 312b, the brush is made up of a plurality of individual bristles or sets of bristles, having their centers affixed to the shaft by being locked between the two or more wires of the shaft during the twisting of the wires. Fabrication of such brushes is well known. The diameter of the right circular cylindrical brushing surface of brush 314b of FIG. 4a is illustrated as D. As mentioned, the diameters D of the brushes of the various members of the set 310 vary from member to member. For example, the diameter D of brush 310b might be about 2.2 mm, the equivalent diameter of the brush 314a of lumen cleaning device 310a might be about 2.0 mm, and the diameter of the brush 314c of lumen cleaning device 310c might be about 3.2 mm. The diameters of the brushes of other members (not illustrated) of set 310 would lie between 2.2 and 3.2 mm.

According to a further aspect of the invention, a swab illustrated as 316b is mounted at or near the second end of shaft 312b of FIG. 4a. As illustrated, swab 316b has a generally cylindrical shape. Swab 316b may be made by placing the swab end of the shaft in a mold, closing the mold, and injecting a liquid material which cures around, and adheres to, the shaft. Swab 316b is made from a material which, when cured, is a somewhat elastic deformable material, which tends to return to its original shape after being deformed. Its diameter d is selected to be slightly larger than diameter D of the brush 314b with which it is associated by shaft 312b. Thus, diameter d of swab 316b may have a diameter of 2.25 mm when brush diameter D is 2.2 mm. This dimensioning assures that the elastic material of the swab is somewhat compressed even when used with the largest lumen appropriate for the diameter D of the associated brush. This compression provides a force which tends to hold the exterior surface of the swab in contact with the interior surface of the lumen, to better remove the film.

According to a further aspect of the invention, the shaft of each lumen cleaning device of set 310 is marked to identify its diameter. The determination of the diameter of such small brushes and swabs may be difficult in the absence of such markings, because a caliper placed over either the brush or the swab may tend to compress it, and give an erroneous reading. Also, it will be difficult to tell when a caliper makes contact with a soft surface such as a brush or swab. FIG. 4a illustrates dimension markings in the form of color-coded paint marks 410 placed in an annular form on the shaft 312b near the brush, and also near the swab, where at least one mark will be visible almost continuously before and during use.

Figure 4B:
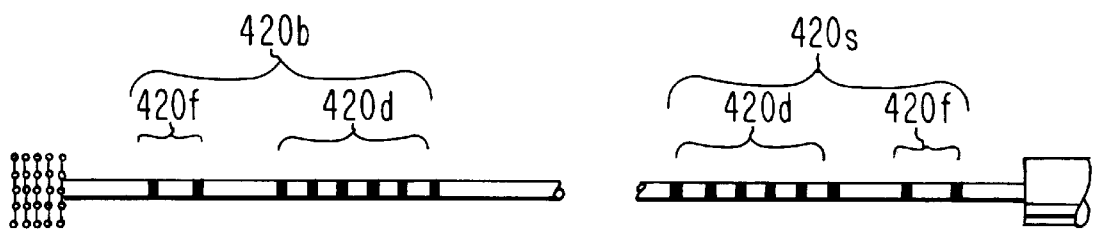

However, color codes require that a key be available, or that the user memorize the color code key. A color code key which is not a part of the lumen cleaning device is likely not to be available when needed, and the key cannot be placed on a tag, because the tag must necessarily be removed before the device is placed in use. This can be somewhat ameliorated by using some conventional color conversion code, such as the code used in electronic work to identify resistors. According to a further aspect of the invention, the dimension code is in the form of sets of bands or annuli of pigment on the shaft, as illustrated in FIG. 4b. In FIG. 4b, the markings adjacent each the brush end of the shaft are designated 420b, and the markings adjacent the swab end of the shaft are designated 420s. Each set of markings is divided into two sub-sets. More specifically, set of markings 420b is subdivided into a first set 420f, which represents the first number of the dimension in millimeters, and a second set 420d represents the decimal value following the value represented by markings 420f. Thus, in FIG. 4b, first subset 420f has two markings or bands, representing the number "two," while the second or decimal number contains six bands, and represents the decimal number "six." With this information, it is possible to establish that the numeric designation is the number "2.6," which represents the diameter of this particular brush, measured in millimeters. The corresponding markings 420f and 420d associated with marking set 420s have the same meaning. The markings on each member of the set, of course, correspond with the dimensions of the associated brushes.

FIG. 5a illustrates a catheter 510 with a lumen which is to be cleaned, and also illustrates the set of lumen cleaning devices 310. The diameter of the lumen to be cleaned is determined by recourse to the literature associated with the catheter, by markings on the catheter, which are suggested by the symbols 550 in FIG. 5a, or by direct measurement. With the diameter measurement information available, the appropriate one of the lumen cleaning devices is selected from set 310, as suggested by arrow 552, using the number code on the shaft of the brush.

FIG. 5b represents the dipping of the brush 314c of the selected one of the lumen cleaning devices, namely device 310c, into a pool 505 of cleaning or sterilizing solution, for those cases in which the lumen to be cleaned is not full of such solution. The brush will tend to hold some of the solution between its bristles.

FIG. 5c represents by a double-headed arrow 508a the pushing and pulling of the brush 314c of the selected one of the lumen cleaning devices, namely device 310c, though the lumen 522 of the catheter to be cleaned. During one pass, the brush is advanced until it exits from the remote end of the lumen, as illustrated, so as to push any particulate matter from the lumen. If the brush has previously been sufficiently wetted with the cleaning solution, no further solution may be required. However, it is possible to run additional cleaning or sterilizing fluid into the lumen being cleaned, as by using a hypodermic-type syringe, illustrated as 530 in FIG. 5c, to place droplets 532 of solution onto the shaft of the cleaning device near its entrance into the lumen, and allowing the droplets to run into the lumen. Alternatively, the syringe can be used to directly inject the solution into the lumen.

The brush 314c of the lumen cleaning device 310c is removed from the lumen being cleaned after the cleaning step illustrated in FIG. 5c, and the swab end of the device is dipped into the solution, as suggested by FIG. 5b, with the positions of the brush 314c and the swab 316c reversed. The swab end of the device is then introduced into the distal end of the lumen, and swabbing is accomplished by back-and-forth movement of the shaft, as illustrated by the double-headed arrow 508b. As in the case of the brushing, additional fluid may be flowed into the lumen during the swabbing.

Figure 5E:
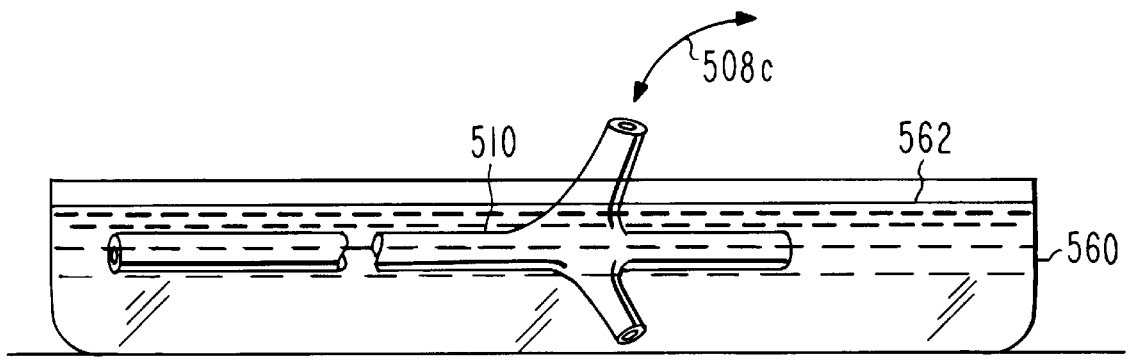

FIG. 5e illustrates another way to introduce cleansing andor sterilizing fluid into the lumen being cleaned during brushing or swabbing. In FIG. 5e, the length of a principal portion of the catheter 510 being cleaned is submerged partially (as illustrated) or completely in a container or pan 560 of cleansing andor sterilizing fluid 562. This submersion occurs during the process of brushing or swabbing, illustrated in FIG. 5e by the arrow 508c. The brushing or swabbing may, of course, be performed from either the distal or the proximal ends of the catheter, or from the nexus of the distal diagnostic end, or at the proximal umbilical end, as the design of the endoscope may allow or require.

Figure 6:
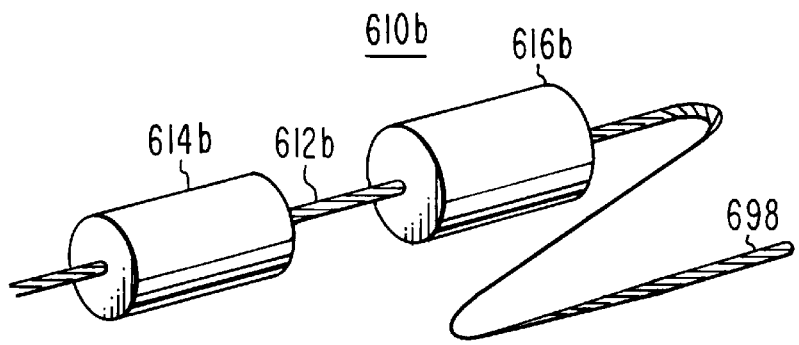
FIG. 6 is a simplified illustration of a cleaning member of another set of cleaning members according to an aspect of the invention.

FIG. 6 illustrates a member 610b of a different set of lumen cleaning devices. As illustrated in FIG. 6, shaft 612b of member 610b is made up of two or more flexible metallic wires, twisted together to form a flexible shaft. At the brush end of the shaft 612b, the brush 614b is made up of a plurality of individual bristles or sets of bristles (not separately illustrated in FIG. 6), as in the arrangement of FIG. 4a. According to an aspect of the invention, a swab illustrated as 616b is mounted on the shaft 612b at a location between the brush location and a second end 698 of the shaft, so that the swab is located closer to the second end of the shaft than the brush. When lumen cleaning device 610b, or any other member of its set (no other members illustrated) are used to clean a lumen, introducing and advancing the brush end of the device into and through the lumen causes the swab to follow. Thus, a complete swipe of the brush and swab can be accomplished almost as readily as a swipe of the brush alone, and is more likely to result in a satisfactory cleaning than in a case in which the cleaning operation is rushed using only a general-purpose brush, and only one swipe is made. The brush and swab diameters of the embodiment of FIG. 6 are dimensioned as described in conjunction with FIGS. 3–5e.

Figure 7A:
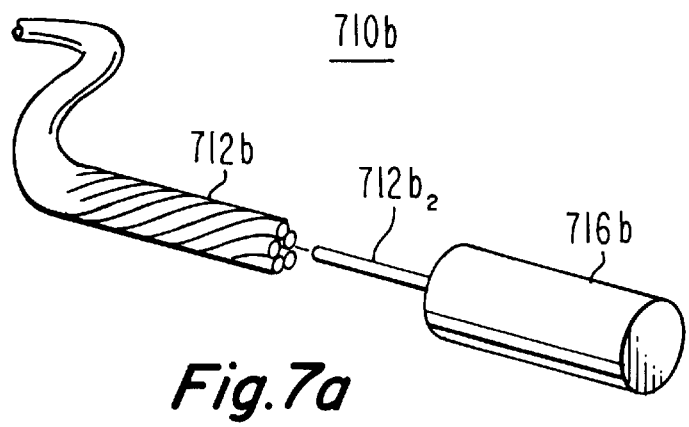
FIG. 7a is a simplified representation of the swab end of a cleaning member similar to that of FIG. 4a, in which the swab is mounted on an add-on of the shaft.
Figure 7B:
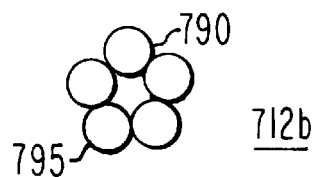
FIG. 7b illustrates the end of a five-wire shaft showing a central aperture.

FIG. 7a illustrates one end of a shaft 712b of a cleaning member 710b of a set of cleaning members (members other than 710b not illustrated), namely that end of the shaft opposite to the end to which a brush is affixed. Thus, the illustrated end of shaft 712b is the "second" or "swab" end. Shaft 712b is made of five twisted wires, as known, with the result that an end view of the shaft 712b is as illustrated in FIG. 7b. As illustrated in FIG. 7b, the shaft is composed of five wires, one of which is designated 790, and which together form a pentagonal arrangement which leaves an aperture 795 at its center. According to an aspect of the invention, the swab 716b is formed about an extension or portion 712b$_2$ of the shaft 712b, which is dimensioned to mount within aperture 795. The shaft extension or portion 712b$_2$ protrudes beyond at least one end of the swab 716b so that the protruding portion may be inserted into the aperture. It may be fastened by a force fit, by adhesive, by welding, or in any suitable manner, whereupon the shaft extension becomes a part of the shaft. In any case, once assembled, the swab is mounted about the shaft, as in the arrangement of FIG. 4a.

A method (FIGS. 5a–5e) for cleaning a lumen (522) of a medical device, such as a catheter (510), which is adapted for introduction into a vas of the body of a patient, where the lumen has a diameter lying in the range of about 2.0 to about 3.2 millimeters, includes the step of providing a set (310) of endoscope lumen cleaning devices (310a, 310b, . . . , 310c). The set (310) of lumen cleaning devices includes a plurality of members, and each member of the set of the lumen cleaning devices includes a shaft (312), a brush (314), and a swab (316). The shaft (312) is elongated and flexible, and defines a brush end and a second end. The shaft (312) has a diameter which is less than 1.8 mm, and preferably no greater than about one and one-half millimeters, and a length greater than about 110 centimeters. The brush (314) is a bristle brush affixed to the shaft (312) near the brush end of the lumen cleaning device (310), with the bristles (314b) of the brush being radially disposed relative to the shaft. The tips of the brush bristles define or provide a circumferential brushing surface defining a diameter (D). The swab (316) surrounds the shaft (312) either near the second end of the lumen cleaning device (310), or at a location on the shaft which is closer to the second end of the shaft. The swab (316) is made from a material which is elastically deformable. The bristles of the brush (314) define one of a plurality of discrete brush diameters in each of the members of the set (310) of lumen cleaning devices. The various members (310a, 310b, ..., 310c) of the set (310) have brush diameters which range in discrete steps from about 2.0 to about 3.2 millimeters. The swab (316) of each of the members of the set (310) of lumen cleaning devices (310a, 310b, ..., 310c) has an outer diameter (d) which is no less than the diameter (D) of its corresponding brush. Thus, each member of the set of lumen cleaning devices includes a brush which is approximately matched to the diameter of the lumen to be cleaned, and a swab which has a diameter which is related to the diameter of its associated brush.

The cleaning method includes the steps of selecting a cleaning device from the set (FIG. 5a), where the brush diameter of the selected one of the cleaning devices is the smallest one of the set which is larger than the diameter of the lumen to be cleaned. Thus, the brush will always be slightly larger than the lumen in which it is used, but only slightly larger. The lumen is brushed with the selected brush (FIG. 5c). Cleansing (including disinfectant) fluid may be introduced in conjunction with the brushing. The brushing may remove most particulate matter from the lumen, but a film of matter may remain, which in general cannot be seen because it is within the small lumen. The brush end of the lumen cleaning device is removed or allowed to exit from the lumen, and the swab is introduced (FIG. 5d) if not already within the lumen, and the lumen is swabbed, again in conjunction with cleansing fluid if desired. The swabbing tends to remove the remaining film.

The brushes may have diameters which increase in diameter in a linear manner from member to member of the set, as for example by having approximate diameters which include 2.0, 2.2, 2.4, ..., 3.0, 3.2 millimeters, where the incremental diameter from member to member of the set is about 0.2 mm. Another increment scheme is that of a geometric increase in diameter, such as an approximate 10% increase in diameter from one member to another, which gives diameters including about 2.0, 2.2, 2.4, 2.7, 3.0, and 3.3. millimeters.

The brushing and swabbing may be accompanied by the use of liquid cleansing or disinfecting material, as by introducing the liquid into the lumen by submerging the endoscope in the liquid cleansing material (FIG. 5e), by pouring or otherwise introducing the material into the lumen during brushing or swabbing (FIG. 5c), or by dipping the brush or swab (FIG. 5b) into the liquid before introduction into the lumen.

A set of lumen cleaning devices according to the invention includes a plurality of members of the set. Each member of the set of lumen cleaning devices includes an elongated, flexible shaft having a diameter not exceeding 1.8 mm, and preferably no greater than one and one-half millimeters in diameter, and having a length of more than 110 centimeters. The shaft defines a brush end and a second end. A brush is affixed to the shaft near the brush end of the shaft. The brush includes a plurality of bristles affixed to the shaft, the tips of which, together, define a right circular cylindrical brushing surface generally centered on the shaft. The cylindrical brushing surface (or the diameter of the brush from tip to tip of the bristles) defines a diameter lying in the range of about 2.0 to about 3.2 millimeters. The diameter of the brush is different among the different members of the set of lumen cleaning devices. For example, a first member of the set of lumen cleaning devices might have a brush diameter of about 2.0 mm, another member of the set might have a brush diameter of about 2.2 mm, and so forth. A swab is affixed to, and surrounds, the shaft near its second end in one embodiment, or at a location closer to the second end in another embodiment. The swab is made from a deformable elastic material such as elastomer foam. The swab may be attached to the shaft by being molded about the shaft, whereby its structure fills the interstices in the shaft. The swab defines a right circular swabbing surface, which is generally centered on the shaft. The diameter of the swabbing surface of the swab is no less than the diameter of the brushing surface. A particular set of lumen cleaning devices has members of the set having brush diameters of about 2.0, 2.4, 2.8, and 3.2 millimeters. Another possible set has brush diameters of about 2.0, 2.2, 2.4, and 2.7 millimeters, and this set may further include brushes having diameters of about 3.0 and 3.2 mm.

Figure 8A:
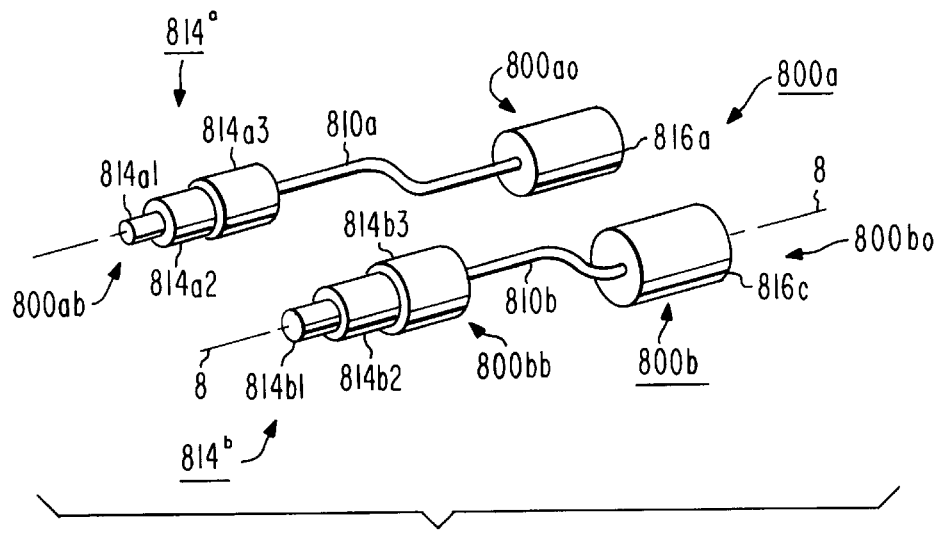
FIG. 8a is a simplified perspective or isometric view of a version of lumen cleaning devices according to another incarnation of the invention, in which the brushes are stepped in diameter, and the swab has a diameter equal to the maximum diameter of the brush.

In FIG. 8a, two different lumen cleaning devices 800a and 800b each include stepped brushes. Lumen cleaning device 800a includes a shaft 810a defining a brush end 800ab and a second or other end 800ao. At the brush end 800ab of lumen cleaning device 800a, a set 814$^a$ of a plurality of brushes 814a1, 814a2, and 814a3 is affixed to the shaft 810a. As illustrated in FIG. 8a, the set 814$^a$ of brushes includes three brushes, designated 814a1, 814a2, and 814a3. The smallest diameter brush of set 814$^a$, namely brush 814a1, is located closest to the brush end 800ab of the lumen cleaning device 800a. The next larger diameter brush, namely brush 814a2, is juxtaposed with smallest-diameter brush 814a1, and the largest-diameter brush of those illustrated, namely brush 814a3, is juxtaposed with brush 814a2, and lies farthest from, or most remote from, brush end 800ab of cleaning device 800a. As also illustrated in FIG. 8a, a swab 816a is affixed to shaft 810a at or near the other end 800ao of the lumen cleaning device 800a. Similarly, lumen cleaning device 800b includes a shaft 810b defining a brush end 800bb and a second or other end 800bo. At the brush end 800bb of lumen cleaning device 800b, a set 814$^b$ of a plurality of brushes 814b1, 814b2, and 814b3 is affixed to the shaft 810a. As illustrated in FIG. 8a, the set 814b of brushes includes three brushes, designated 814b1, 814b2, and 814b3. The smallest diameter brush of set 814$^b$, namely brush 814b1, is located closest to the brush end 800bb of the lumen cleaning device 800b. The next larger diameter brush, namely brush 814b2, is juxtaposed with smallest-diameter brush 814b1, and the largest-diameter brush of those illustrated, namely brush 814b3, is juxtaposed with brush 814b2, and lies farthest from, or most remote from, brush end 800bb of cleaning device 800b. The diameters of brushes or brush segments 814b1, 814b2, and 814b3 differs from the diameters of brushes or brush segments 814a1, 814a2, and 814a3. More particularly, the diameter of brush 814b1 is larger than the diameter of brush 814a1, brush 814*b*2 has a larger diameter than brush 814*a*2, and brush 814*b*3 has a larger diameter than brush 814*a*3. As also illustrated in FIG. 8*a,* a swab 816*b* is affixed to shaft 810*b* at or near the other end 800*bo* of the lumen cleaning device 800*b.*

Figure 8B:
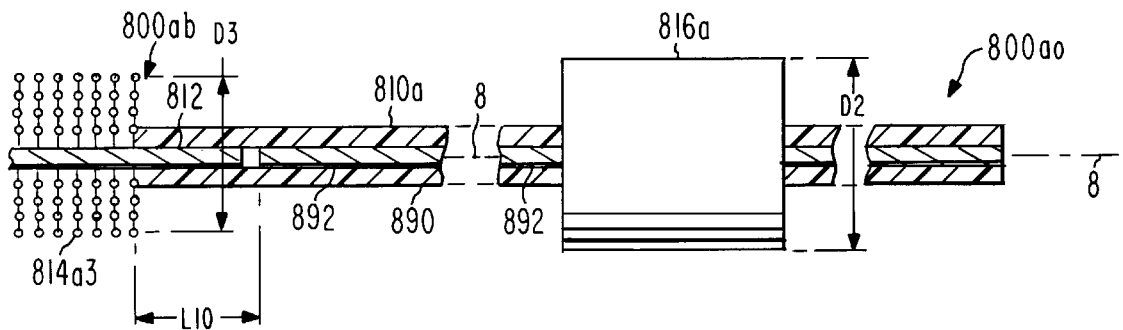

FIG. 8*b* is a cross-sectional view of a portion of lumen cleaning device 800*a* of FIG. 8*a.* In FIG. 8*b,* shaft 810*a* includes, over most of its length, a central core or support 892, in the form of a twisted metallic wire, which may be stainless steel. Since the lumen cleaning device may be a single-use device, cost is an important factor, and inexpensive metals, or nonmetallic materials, may also be used for support. A polymeric tube 890, which is preferably a polyethylene tube, extends over the core 892. As illustrated, core 892 is shorter than the tube 890, with the result that a length of the tube 890, identified as length L10, does not contain core material 892. Thus, the tube 890 contains a "non-core" portion of its lumen in region L10. This non-core region is provided to allow the brush or brushes to be affixed to the shaft. In FIG. 8*b,* a portion of largest-diameter brush 814*a*3 is illustrated, mounted on a stub shaft 812. As illustrated, stub shaft 812 fits into non-core portion L10 of the tube, and is adhesively or fusion bonded to the tube, to firmly affix the brushes to the shaft 810*a.* As also illustrated in FIG. 8*b,* swab 816*a* has a diameter $D_2$ greater than, or at least no less than, that of the largest diameter $D_3$ of brush or brush segment 814*a*3.

Figure 9:
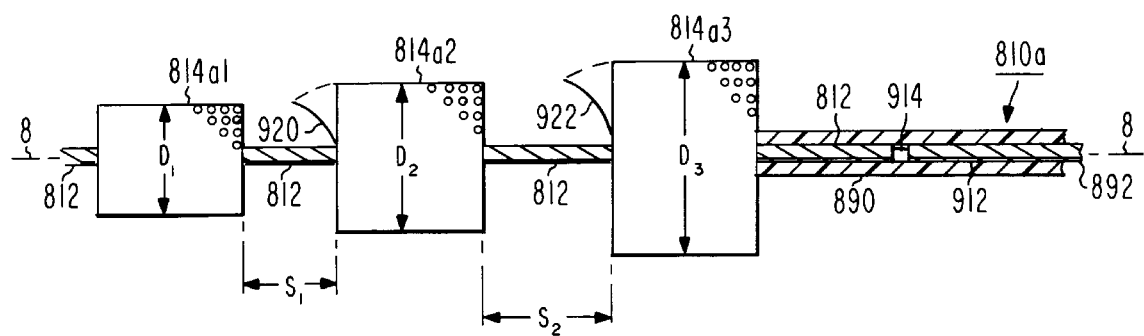
FIG. 9 is a simplified cross-sectional view of the brush end of another version of the invention similar to that of FIGS. 8a and 8b, in which the stepped brushes are separated by non-brush spaces, and also illustrating a method for attachment of the brush(es) to the shaft.

In FIG. 9, a lumen cleaning device according to an aspect of the invention includes a shaft 810*a* with a twisted-wire metallic core 892 within a polymeric tube 890, all centered on a local longitudinal axis 8. A set of three brushes 814*a*1, 814*a*2, and 814*a*3 is mounted on a stub shaft 812, an end of which is inserted into polymeric tube 890, leaving a gap 914 between the stub shaft 812 and the core 892. The brushes are separated from each other by spaces S1, S2, which have axial dimensions selected to prevent the bristles of the larger of two adjacent brushes from overlapping onto the brushing surface of the smaller of the two adjacent brushes. More particularly, mutually adjacent brushes 814*a*1 and 814*a*2 are spaced apart by S1, a region without bristles (or at least without bristles as long as those of brush 814*a*1), and mutually adjacent brushes 814*a*2 and 814*a*3 are separated by space S2. In space S1, a bent-over bristle 920 from that edge of brush 814*a*2 which is adjacent to space S1 is illustrated as being bent over to the diameter $D_1$ of brush 814*a*1, as would happen if the lumen cleaning device of FIG. 9 were being pulled through a lumen with diameter $D_1$, with brush 814*a*3 leading brush 814*a*1. As illustrated, the space S1 is long enough so that the bristle 920 does not reach as far as the brushing surface of brush 814*a*1, so the bristles of the larger brush cannot affect the brushing performance of the smaller brush when cleaning a lumen for which the smaller brush is dimensioned. Similarly, mutually adjacent brushes 814*a*2 and 814*a*3 are spaced apart by S2, a region without bristles, and mutually adjacent brushes 814*a*2 and 814*a*3 are separated by space S2. In space S2, a bent-over bristle 922 from that edge of brush 814*a*3 which is adjacent to space S2 is illustrated as being bent over to the diameter $D_2$ of brush 814*a*2, as would happen if the lumen cleaning device of FIG. 9 were being pulled through a lumen with diameter $D_2$, with brush 814*a*3 leading brush 814*a*2. As illustrated, the space S2 is long enough so that the bristle 922 does not reach as far as the brushing surface of brush 814*a*2, so the bristles of the larger brush cannot affect the brushing performance of the smaller brush when cleaning a lumen for which the smaller brush is dimensioned.

Figure 10:
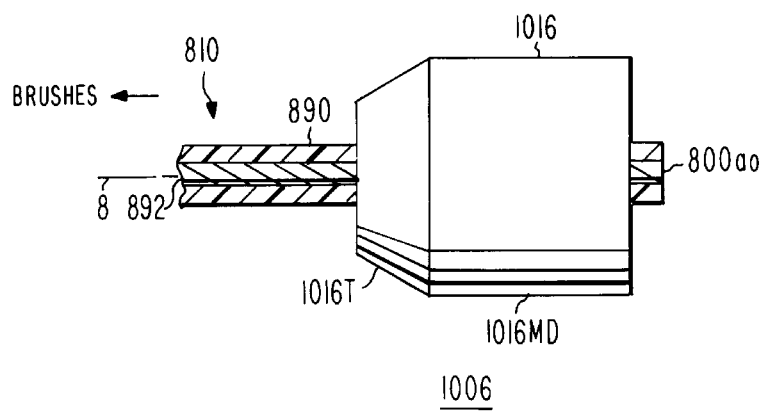
FIG. 10 is a simplified cross-sectional view of a swab having a tapered portion, which may be used in any of the embodiments of FIGS. 3, 4a, 4b, 5a, 5b, 5c, 6, 7a, 8a, or 8b.

FIG. 10 is a side, partially cross-sectional view of the swab end of a lumen cleaning device according to an aspect of the invention. In FIG. 10, the swab 1016 is located almost at the swab end 800*ao* of the shaft 810. As in other illustrations, the shaft 810 is made up of a polymeric tube 890 with a core 892. As illustrated in FIG. 10, swab 1016 includes a portion 1016MD having the maximum diameter selected, as described above, to equal or exceed the maximum diameter of the associated brush(es), which are not illustrated in FIG. 10. Swab 1016 also includes a tapered portion 1016T, which is tapered from the maximum diameter to a smaller diameter. The tapered portion is located closer to the brush end of the lumen cleaning device than to the swab or other end, so that the swab may be easily inserted into the lumen to be cleaned, when that lumen is smaller than the maximum diameter of the swab.

Figure 11:
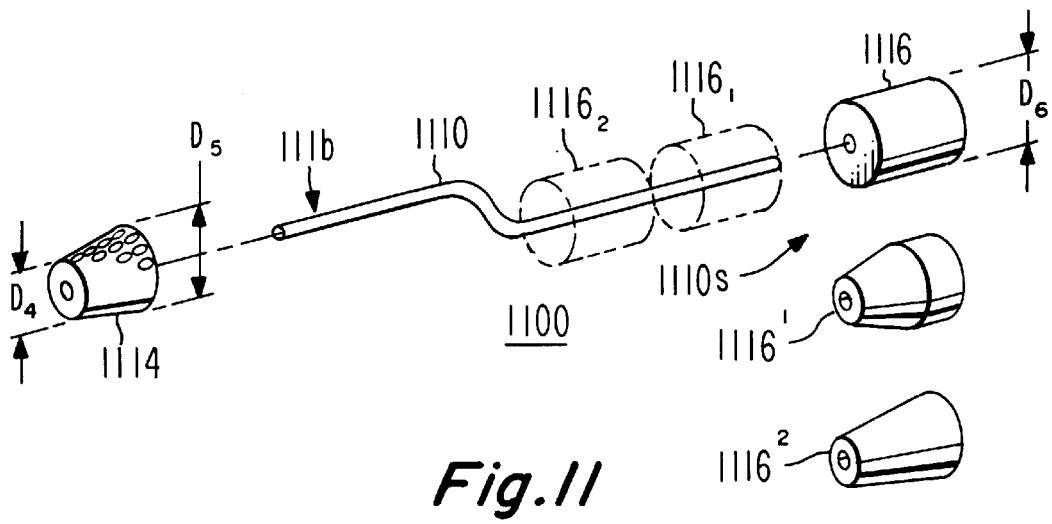
FIG. 11 is an exploded view of an embodiment of a lumen cleaning device in accordance with an aspect of the invention in which the brush is tapered, and in which the swab may be tapered.

FIG. 11 illustrates another incarnation of the invention, in which the brush is tapered, and in which the taper is oriented in such a manner as to allow the brush end of the lumen cleaning device to be inserted into a lumen to be cleaned. More particularly, lumen cleaning device 1100 of FIG. 11 includes a flexible shaft 1110 defining brush end 1110*b* and second end 1110S. A brush 1114 has a shape corresponding to the frustum (also known as frustrum) of a cone, namely a portion or section of a cone, with parallel ends, which are orthogonal to the axis of the defining cone. In FIG. 11, brush 1114 has a smaller diameter $D_4$ closer (when the brush is assembled to the shaft) to the brush end of the lumen cleaning device, and also has a larger diameter $D_5$ more remote from the brush end of the shaft than other portions of the brush. Also in FIG. 11, a swab 1116 in the form of a right circular cylinder is affixed to shaft 1110 at the location illustrated as 1116$_1$. An alternative location for swab 1116 is illustrated as 1116$_2$, which lies between brush 1114 and the second end 1110S of the shaft. FIG. 11 also illustrates two different configurations which the swab may take. Thus, the swab illustrated as 1116$^1$ includes a tapered portion and a cylindrical portion, similar to the swab of FIG. 10. Swab 1116$^2$ has only a tapered portion, but the largest-diameter portion of the tapered portion has a diameter equal to or greater than that of the largest portion of the brush.

According to another aspect of the invention, it is recognized that once the brush is pushed through the lumen being cleaned, the brush, and especially the leading edge of the brush, may be soiled with matter. If the brush is drawn back through the lumen in a retrograde direction after the first passage through the lumen, material may be redeposited in the lumen. This redeposited material may reduce the effectiveness of the swab. According to an aspect of the invention, therefore, a method for cleaning a lumen of a catheter includes the step of advancing the brush end of a lumen cleaning device through the lumen being cleaned, until the brush exits from the remote end of the lumen. Rather than pulling the brush back through the lumen, the brush end of the lumen cleaning device is pulled, to thereby draw the swab through the lumen, without the now-soiled brush returning through the lumen. This step may be repeated, but only with a fresh, or freshly cleaned, lumen cleaning device.

FIG. 12 tabulates the preferred range of brush diameters and swab diameters for cleaning the biopsy channel and suction channel lumens (or of other lumens) of catheters, where the lumens of a particular catheter have the given dimensions of biopsy channel and suction channel. As a first example, the portion of FIG. 12 headed "ORIGINAL" tabulates the brush and swab dimensions for individual lumen cleaning devices of a set of lumen cleaning devices, such as those described in conjunction with FIGS. 3 and 4*a.* Entering the tabulation at a biopsy channel lumen diameter of 2.4 mm, with a suction channel lumen diameter of 3.7 mm, the appropriate brush has a fixed brush diameter of 2.6 mm and a swab diameter of 2.6 mm. It will be noted that each different lumen diameter requires a different cleaning brush and swab dimension from other lumen diameters. In that portion of FIG. 12 headed "Tapered," a cleaning device with a brush diameter ranging from 2.2 to 4.1 mm will clean three different catheters, namely the first three listed in the Tapered section. Similarly, a cleaning device having brush dimensions tapering from 3.1 to 4.1 mm is satisfactory for cleaning catheters with biopsy channel lumens extending from diameters of 2.8 mm to 3.5 mm, with suction channel diameters of 3.7 mm. A single-diameter brush of 4.1 mm is all that is required for catheters having biopsy channels of 3.7 to 3.8 mm and suction channels of 3.7 mm. A tapered brush 4.1 mm to 4.6 mm, with a 4.6 mm swab, is suitable for a catheter having a biopsy channel lumen diameter of 4.2 mm and a suction channel lumen diameter of 3.7 mm. In that portion of FIG. 12 headed "Stepped," two-brush embodiments are contemplated, and, for example, a stepped brush having diameters of 2.2 and 4.1 mm, and a swab of 4.1 mm, is suitable for a catheter in which the biopsy lumen has a diameter of 2.0 mm and a suction channel lumen diameter of 3.7 mm. Similarly, a stepped brush having diameters of 3.5 and 4.1 mm, and a swab of 4.1 mm, is suitable for a catheter in which the biopsy lumen has a diameter of 3.2 mm and a suction channel lumen diameter of 3.7 mm. Other values can be derived from the table of FIG. 12.

Other embodiments of the invention will be apparent to those skilled in the art. For example, the bristles of the brush may be of natural or synthetic materials. While the bristles have been described as being held to the shaft by being pinched between (or among) the twisted wires which make up the shaft, other attachment methods may be used, such as adhesives. The wires of the shaft may be made of metal, such as stainless steel for its corrosion resistance, or of any other material having appropriate properties of flexibility and strength. While the swab has been described as being formed by injecting liquid into a mold and allowing the liquid to cure, it can be made by a number of methods, including the carving or machining of the swab from bulk stock, making a hole in its body, placing adhesive on the swab end of the shaft, and inserting the adhesive-coated end of the shaft into the hole in the swab. The material of the swab may be foamed material, either closed-cell or open-cell, with the open-cell being preferred as presenting a rougher surface, to aid in removal of film, while the closed-cell foam is easier to clean, and improves the reusability of the cleaning device. While the cleaning andor sterilizing liquid has been referred to as a solution, it may be any liquid, or even a fluid, having appropriate cleansing or disinfecting properties. While the methods for holding the brush and the swab to the shaft have identical to each other in the illustrated embodiments, which is to say (a) both the brush and the swab mounted directly onto the shaft, (b) both the brush and the swab mounted on stub shafts inserted into a space between twisted wires of the shaft, or (c) both the brush and the swab mounted on stub shafts inserted into apertures at the ends of a tube surrounding the shaft, any combination or mixture of these three methods (a), (b), and (c) could be used on a single device.

A particular manifestation of the invention lies in a cleaning device (310b) for a lumen (26) of a catheter (10) includes a flexible shaft (312b) having a diameter no greater than about two millimeters. The shaft defines a brush end and a second end. A generally cylindrical brush (314b) is affixed to the shaft near the brush end of the shaft. In this context, "near" includes "at" the brush end. The cylindrical brush (314b) has a diameter (D) of its bristles lying between about 3 and 4 millimeters, for some purposes closer to 5 mm than to 4 mm. The cleaning device includes an elastomeric, generally cylindrical swab affixed to the shaft at a location between the brush and the second end of the shaft. The swab has a diameter no smaller than the diameter (D) of the brush.

A cleaning device (800a, 800b) for a lumen of a catheter includes a flexible shaft (810a, 810b) having a diameter no greater than about two millimeters. The shaft (810a, 810b) defines a brush end (800ab, 800bb) and a second or other end (800ao, 800bo). The cleaning device (800a, 800b) includes a plurality of generally cylindrical brushes (814a1, 814a2, 814a3; 814b1, 814b2, 814b3) affixed to the shaft (810a, 810b) near the brush end (800ab, 800bb) of the shaft (810a, 810b). The cylindrical brushes (814a1, 814a2, 814a3; 814b1, 814b2, 814b3) have diameters lying between about 2 and 5 millimeters. The cleaning device (800a, 800b) further includes an elastomeric, generally cylindrical swab (816a, 816b) affixed to the shaft (810a, 810b) at a location (816a) which lies between the brushes (814a1, 814a2, 814a3; 814b1, 814b2, 814b3) and the second end of the shaft (810a, 810b). The location of the swab (816a, 816b) may be at or near the second end (800ao, 800bo) of the shaft (810a, 810b). The swab (816a, 816b) has a maximum diameter ($D_2$) no smaller than the diameter ($D_3$) of that one (814a3, 814b3) of the plurality of brushes (814a1, 814a2, 814a3; 814b1, 814b2, 814b3) having the largest diameter. In one version of this arrangement, the shaft (810a) defines an axis (8) of elongation, and the brushes (814a1, 814a2, 814a3) are separated from each other, in a direction parallel to the axis of elongation, by "non-brush" regions or space(s) ($S_1$, $S_2$) lacking bristles. The space(s) ($S_1$, $S_2$) have axial lengths related to the radii of those of the brushes (814a1, 814a2, 814a3; 814b1, 814b2, 814b3) which are immediately adjacent to the spaces. More particularly, the space(s) are selected in axial length, so that when the bristles (920; 922) of the larger (814a2; 814a3) of the two adjacent brushes (814a2 relative to 814a1; 814a3 relative to 814a2) are bent over toward the smaller of the adjacent brushes (814a1 relative to 814a2; 814a3 relative to 814a3) when the larger brush precedes the smaller brush through the lumen being cleaned, they do not overlap into the region occupied by the smaller brush. In a particularly advantageous embodiment of the invention, the bristles of the brushes (814a1, 814a2, 814a3; 814b1, 814b2, 814b3) are made from polymer, preferably nylon. A particular version of this avatar is one in which the number of brushes (814a1, 814a2, 814a3; 814b1, 814b2, 814b3) on each shaft (810a, 810b) is two, and the brushes (814a1, 814a2, 814a3; 814b1, 814b2, 814b3) have diameters of about 2.2 mm and 4.1 mm, and the swab 816a, 816b) has a diameter not less than 4.1 mm. Another version, also with two brushes (814a1, 814a2, 814a3; 814b1, 814b2, 814b3), has brush diameters of about 2.4 mm and 4.1 mm, and the swab 816a, 816b) has a diameter not less than 4.1 mm. In other two-brush versions, the brushes (814a1, 814a2, 814a3; 814b1, 814b2, 814b3) have diameters of about 2.65 & 4.1 mm; 3.1 & 4.1 mm; 3.5 & 4.1 mm; 3.85 & 4.1 mm, and in all of these versions the swab 816a, 816b) has a diameter of not less than 4.1 mm. In another version, the number of brushes (814a1, 814a2, 814a3; 814b1, 814b2, 814b3) is two, and the brushes (814a1, 814a2, 814a3; 814b1, 814b2, 814b3) have diameters of about 4.1 mm and 4.6 mm; the swab 816a, 816b) has a diameter not less than 4.6 mm. In any of the above versions, the swab 816a, 816b) may be located closer to the brush end (800ab, 800bb) of the shaft (810a, 810b) than to the second end of the shaft (810a, 810b). In a preferred embodiment, that one of the brushes (814a1, 814a2, 814a3; 814b1, 814b2, 814b3) having the smallest diameter among the brushes (814a1, 814a2, 814a3; 814b1, 814b2, 814b3) is closest to the brush end (800ab, 800bb) of the shaft (810a, 810b). Where there are more than two brushes (814a1, 814a2, 814a3; 814b1, 814b2, 814b3), the brushes (814a1, 814a2, 814a3; 814b1, 814b2, 814b3) preferably arrayed on the shaft (810a, 810b) in such a manner that those of the brushes (814a1, 814a2, 814a3; 814b1, 814b2, 814b3) having a particular diameter are more remote from the brush end (800ab, 800bb) of the shaft (810a, 810b) than all of the brushes (814a1, 814a2, 814a3; 814b1, 814b2, 814b3) having diameters less than the particular diameter. Another particularly advantageous embodiment (1000) is one in which the swab (1016) includes a portion (1016T) with a tapered diameter, and the smallest-diameter portion of the swab (1016) is closer to the brush end (800ab, 800bb) of the shaft (810a, 810b) than that portion (1016MD) of the swab (1016) having the maximum diameter. In this avatar, the preferred shaft (810a, 810b) includes a metallic inner portion (892) or core, surrounded by a polymeric tube (890), which may be, for example, polyethylene.

A cleaning device (1100) for a lumen (22) of a catheter (10) according to another hypostasis of the invention includes a flexible shaft (1110) having a diameter no greater than about two millimeters. The shaft (1110) defines a brush end (1110b), a second end (1110s), and an axis (8) of elongation. A brush (1114), in the form of the frustum of a cone, is affixed to the shaft (1110) near the brush end (1110b) of the shaft (1110), with the axis of the frustum substantially coincident with the axis (8) of elongation. The brush (1114) has a smallest diameter ($D_4$) of about 2 millimeters, and a largest diameter less than about 5 millimeters. The cleaning device (1100) includes an elastomeric, generally cylindrical swab (1116) affixed to the shaft (1110) at a location ($1116^1$, $1116^2$) between the brush (1114) and the second end (1110S) of the shaft (1110). The swab (1116) has a diameter ($D_6$) no smaller than the largest diameter ($D_5$) of the brush (1114). For cleaning catheters (10) having biopsy channel lumens in the range of about 2.0 to 2.4 mm in diameter and suction channel lumens in the range of about 3.7 mm, the tapered brush (1114) has a diameter ranging from about 2.2 to about 4.1 mm, and a swab (1116) diameter of about 4.1 mm. For cleaning catheters having biopsy channel lumens in the range of about 2.8 to 3.5 mm in diameter and suction channel lumens in the range of about 3.7 mm, the tapered brush (1114) has a diameter ranging from about 3.1 to about 4.1 mm, and a swab (1116) diameter of about 4.1 mm. For cleaning catheters having biopsy channel lumens with a diameter of about 4.2 mm and suction channel lumen in the range of about 3.7 mm, the tapered brush (1114) has a diameter ranging from about 4.1 to about 4.6 mm, and a swab (1116) diameter of about 4.6 mm. For cleaning catheters having biopsy channel lumens in the range of about 3.7 to 3.8 mm and suction channel lumens in the range of about 3.7 mm, the brush (1114) is not tapered, but has a diameter of about 4.1 mm, and a swab (1116) diameter which is also about 4.1 mm. The shafts (1110) of these embodiments are at least 100 cm long, and preferably greater than 110 cm.

What is claimed is:

1. A cleaning device for the lumen of a catheter, said cleaning device comprising:
    a flexible shaft having a diameter no greater than about 1.8 millimeters, said shaft defining a brush end and a second end;
    a generally cylindrical brush affixed to said shaft near said brush end of said shaft, said cylindrical brush having a diameter lying between about 2.0 and 3.2 millimeters; and
    an elastomeric, generally cylindrical swab affixed to said shaft at a location between said brush and said second end of said shaft, which location may include said second end of said shaft, said swab having a diameter no smaller than said diameter of said brush.

2. A device according to claim 1, wherein said swab is located closer to said brush end of said shaft than to said second end of said shaft.

3. A method for cleaning a lumen of a medical device adapted for introduction into a vas of the body of a patient, where said lumen has a diameter lying in the range of about 2.0 to about 3.2 millimeters, said method comprising the steps of:
    providing a set of endoscope lumen cleaning devices, which set of lumen cleaning devices includes a plurality of members, each member of said set of said lumen cleaning devices including (a) an elongated, flexible shaft defining a brush end and a second end, and having a diameter which is less than about 1.8 millimeters and a length greater than about 110 centimeters, (b) a bristle brush affixed to said shaft at a location near said brush end of said lumen cleaning device, said bristles of said brush being radially disposed relative to said shaft, to provide a circumferential brushing surface, and (c) a swab surrounding said shaft at a location closer to said second end than said location of said brush is to said second end of said shaft, said swab being made from a material which is elastically deformable, (d) said bristles of said brush defining one of a plurality of discrete brush diameters in each of said members of said set of lumen cleaning devices, which plurality of discrete brush diameters range from about 2.0 to about 3.2 millimeters, (e) said swab of each of said members of said set of lumen cleaning devices having an outer diameter which is no less than said diameter of said one of said plurality of said discrete brush diameters;
    selecting from among said members of said set of lumen cleaning devices that one of said members in which said diameter of said brush is no less than the diameter of said lumen which is to be cleaned;
    brushing said lumen to be cleaned, by introducing into an end of said lumen to be cleaned the brush end of said one of said members, and passing said brush of said one of said members completely through said lumen at least once, so that said brush of said one of said members exits the remote end of said lumen, whereby large particles of matter tend to be removed from said lumen, but some film may remain at some locations within said lumen to be cleaned;
    swabbing said lumen to be cleaned, by introducing said swab of said lumen cleaning device into an end of said lumen to be cleaned, and passing said swab of said one of said members completely through said lumen to be cleaned at least once.

4. A method according to claim 3, wherein said providing step includes the step of providing lumen cleaning devices having brush diameters of about 2.0, 2.2, 2.4, 2.7, 2.9, and 3.2 millimeters.

5. A set of lumen cleaning devices including a plurality of members, each member of said set of lumen cleaning devices including:
    an elongated, flexible shaft having a diameter not exceeding 1.8 millimeters in diameter, and having a length of more than 110 centimeters, said shaft defining a brush end and an opposite end;
    a brush affixed to said shaft at a location near said brush end of said shaft, said brush including a plurality of bristles affixed to said shaft, and defining a right circular cylindrical brushing surface generally centered on said shaft, said cylindrical brushing surface defining a diameter lying in the range of about 2.0 to about 3.2 millimeters, which diameter is different among the different members of said set of lumen cleaning devices;

a swab affixed to and surrounding said shaft at a location closer to said opposite end of said shaft than said location of said brush, said swab being made from a deformable elastic material, and defining a right circular swabbing surface generally centered on said shaft, the diameter of said swabbing surface of said swab being no less than said diameter of said brushing surface.

6. A set of lumen cleaning devices according to claim 5, wherein said diameters of said brushing surfaces of various members of said set include diameters of 2.0, 2.4, 2.8, and 3.2 millimeters.

7. A set of lumen cleaning devices according to claim 5, wherein said diameters of said brushing surfaces of various members of said set include diameters of 2.0, 2.2, 2.4, and 2.7 millimeters.

8. A set of lumen cleaning devices according to claim 7, wherein said diameters of said brushing surfaces of various members of said set include diameters of 3.0 and 3.2 millimeters.

9. A set of lumen cleaning devices according to claim 5, wherein said location of said swab is near said opposite end of said shaft.

10. A method for cleaning a lumen of a medical device adapted for introduction into a vas of the body of a patient, where said lumen has a diameter lying in the range of about 2.0 to about 3.2 millimeters, said method comprising the steps of:

providing a set of endoscope lumen cleaning devices, which set of lumen cleaning devices includes a plurality of members, each member of said set of said lumen cleaning devices including (a) an elongated, flexible shaft defining a brush end and a swab end, and having a diameter which is less than about 1.8 millimeters and a length greater than about 110 centimeters, (b) a bristle brush affixed to said shaft near said brush end of said lumen cleaning device, said bristles of said brush being radially disposed relative to said shaft, to provide a circumferential brushing surface, and (c) a swab surrounding said shaft near said swab end of said lumen cleaning devices, said swab being made from a material which is elastically deformable, (d) said bristles of said brush defining one of a plurality of discrete brush diameters in each of said members of said set of lumen cleaning devices, which plurality of discrete brush diameters range from about 2.0 to about 3.2 millimeters, (e) said swab of each of said members of said set of lumen cleaning devices having an outer diameter which is equal to said one of said plurality of said discrete brush diameters;

selecting from among said members of said set of lumen cleaning devices that one of said members in which said diameter of said brush is no less than the diameter of said lumen which is to be cleaned;

brushing said lumen to be cleaned, by introducing into an end of said lumen to be cleaned the brush end of said one of said members, and passing said brush of said one of said members completely through said lumen at least once, so that said brush of said one of said members exits the remote end of said lumen;

in conjunction with said step of brushing said lumen, introducing liquid cleansing material into said lumen, whereby said brushing step is performed in the presence of said cleansing material, whereby large particles of matter tend to be removed from said lumen, but some film may remain at some locations within said lumen to be cleaned;

removing said brush end of said one of said members from said lumen to be cleaned;

swabbing said lumen to be cleaned, by introducing into an end of said lumen to be cleaned said swab end of said lumen cleaning device, and passing said swab of said one of said members completely through said lumen to be cleaned at least once, so that said swab exits the remote end of said lumen;

in conjunction with said step of swabbing said lumen, introducing liquid cleansing material into said lumen, whereby said swabbing step is performed in the presence of said cleansing material, whereby said film of matter tends to be removed from said lumen.

11. A method according to claim 10, wherein said brushing step includes the step of repeatedly passing said brush through said lumen in two directions.

12. A method according to claim 11, wherein said step of repeatedly passing said brush includes the step of repeatedly passing said brush in said two directions without allowing said brush to exit from the distal end of said lumen.

13. A method according to claim 10, wherein said swabbing step includes the step of repeatedly passing said swab through said lumen in two directions.

14. A method according to claim 13, wherein said step of repeatedly passing said swab includes the step of repeatedly passing said swab in said two directions without allowing said swab to exit from the distal end of said lumen.

15. A method according to claim 10, wherein one of said steps of introducing liquid cleansing material into said lumen includes the step of submerging said endoscope in said liquid cleansing material.

16. A method according to claim 10, wherein one of said steps of introducing liquid cleansing material into said lumen includes the step of dipping an end of said one of said members of said set of lumen cleaning devices into said liquid cleansing material.

17. A method according to claim 10, wherein one of said steps of introducing liquid cleansing material into said lumen includes the step of pouring said liquid cleansing material into said lumen.

18. A cleaning device for a lumen of a catheter, said cleaning device comprising:

a flexible shaft having a diameter no greater than about two millimeters, said shaft defining a brush end and a second end;

a generally cylindrical brush affixed to said shaft near said brush end of said shaft, said cylindrical brush having a diameter lying between about 3 and 4 millimeters; and an elastomeric, generally cylindrical swab affixed to said shaft at a location between said brush and said second end of said shaft, said swab having a diameter no smaller than said diameter of said brush.

19. A cleaning device for a lumen of a catheter, said cleaning device comprising:

a flexible shaft having a diameter no greater than about two millimeters, said shaft defining a brush end and a second end;

a plurality of generally cylindrical brushes affixed to said shaft near said brush end of said shaft, said cylindrical brushes having diameters lying between about 2 and 4.6 millimeters; and an elastomeric, generally cylindrical swab affixed to said shaft at a location between said brushes and said second end of said shaft, which location may include said second end of said shaft, said swab having a maximum diameter no smaller than the diameter of that one of said brushes having the largest diameter.

20. A cleaning device according to claim 19, wherein:

said shaft defines an axis of elongation; and said brushes are separated from each other by spaces lacking bristles, said spaces having axial lengths related to the radii of those of said brushes which are immediately adjacent said spaces.

21. A cleaning device in accordance with claim 19, wherein bristles of said brushes are made from a polymer.

22. A cleaning device according to claim 19, wherein:

said plurality of brushes is two, and said brushes have diameters of about 2.2 mm and 4.1 mm; and said swab has a diameter not less than 4.1 mm.

23. A cleaning device according to claim 19, wherein:

said plurality of brushes is two, and said brushes have diameters of about 2.4 mm and 4.1 mm; and said swab has a diameter not less than 4.1 mm.

24. A cleaning device according to claim 19, wherein:

said plurality of brushes is two, and said brushes have diameters of about 2.65 mm and 4.1 mm; and said swab has a diameter not less than 4.1 mm.

25. A cleaning device according to claim 19, wherein:

said plurality of brushes is two, and said brushes have diameters of about 3.1 mm and 4.1 mm; and said swab has a diameter not less than 4.1 mm.

26. A cleaning device according to claim 19, wherein:

said plurality of brushes is two, and said brushes have diameters of about 3.5 mm and 4.1 mm; and said swab has a diameter not less than 4.1 mm.

27. A cleaning device according to claim 19, wherein:

said plurality of brushes is two, and said brushes have diameters of about 3.85 mm and 4.1 mm; and said swab has a diameter not less than 4.1 mm.

28. A cleaning device according to claim 19, wherein:

said plurality of brushes is two, and said brushes have diameters of about 4.1 mm and 4.6 mm; and said swab has a diameter not less than 4.6 mm.

29. A cleaning device in accordance with claim 19, wherein said swab is located closer to said brush end of said shaft than to said second end of said shaft.

30. A cleaning device in accordance with claim 19, wherein that one of said brushes having the smallest diameter among said brushes is closest to said brush end of said shaft.

31. A cleaning device in accordance with claim 30, wherein said brushes are arrayed on said shaft in such a manner that those of said brushes having a particular diameter are more remote from said brush end of said shaft than all of said brushes having diameters less than said particular diameter.

32. A cleaning device in accordance with claim 19, wherein said swab includes a portion with a tapered diameter, the smallest-diameter portion of said swab being closer to said brush end of said shaft than that portion of said swab having said maximum diameter.

33. A cleaning device in accordance with claim 19, wherein at least a portion of said flexible shaft includes an inner metallic portion and an outer polymeric portion.

34. A cleaning device in accordance with claim 33, wherein said outer polymeric portion is generally tubular, and said metallic portion lies within the lumen of said tubular portion in a central portion of said shaft, but does not extend to at least one end of said outer polymeric portion, whereby said lumen is not occupied by said metallic portion of said shaft in a vacant lumen portion near said one end of said outer polymeric portion of said shaft.

35. A cleaning device in accordance with claim 34, wherein one of (a) said brushes, considered as a single element, and (b) said swab, is mounted on a stub shaft; and a portion of said stub shaft of said one of said brushes and said swab is located within said vacant lumen portion.

36. A set of lumen cleaning devices including a plurality of members, each member of said set of lumen cleaning devices including:

an elongated, flexible shaft having a diameter not exceeding two millimeters in diameter, and having a length of more than 110 centimeters, said shaft defining a brush end and an opposite end;

a brush affixed to said shaft at a location near said brush end of said shaft, said brush including a plurality of bristles affixed to said shaft, and defining a right circular cylindrical brushing surface generally centered on said shaft, said cylindrical brushing surface defining a diameter lying in the range of about 2 to about 4.6 millimeters, which diameter is different among the different members of said set of lumen cleaning devices;

a swab affixed to and surrounding said shaft at a location which is one of (a) closer to said opposite end of said shaft than said location of said brush and (b) closer to said brush end of said shaft than to said opposite end of said shaft, said swab being made from a deformable elastic material, and defining a right circular swabbing surface generally centered on said shaft, the diameter of said swabbing surface of said swab being no less than said diameter of said brushing surface.

37. A set of lumen cleaning devices according to claim 36, wherein said diameters of said brushing surfaces of various members of said set include diameters of 2.2, 2.4, 2.65, and 4 millimeters.

38. A set of lumen cleaning devices according to claim 36, wherein said diameters of said brushing surfaces of various members of said set include diameters of 2.4, 2.6, 3.1, 3.5, and 4 millimeters.

39. A set of lumen cleaning devices according to claim 38, wherein said diameters of said brushing surfaces of various members of said set include diameters of 2.42, 2.64, 3.08, 3.52 and 4.07 millimeters.

40. A set of lumen cleaning devices according to claim 36, wherein said diameters of said brushing surfaces of various members of said set include diameters of 4.2 and 4.6 millimeters.

41. A set of lumen cleaning devices according to claim 36, wherein said location of said swab is near said opposite end of said shaft.

42. A set of lumen cleaning devices according to claim 41, wherein said location of said swab is at said opposite end of said shaft.

43. A set of lumen cleaning devices according to claim 41, wherein said location of said swab is closer to said brush than to said opposite end of said shaft, but more remote from said brush end of said shaft than said brush.

44. A set of lumen cleaning devices in accordance with claim 36, wherein said swab further includes a portion with a tapered diameter.

45. A set of lumen cleaning devices in accordance with claim 44, wherein said tapered-diameter portion of said swab is more remote from said opposite end of said shaft than a cylindrical portion of said swab.

46. A cleaning device for a lumen of a catheter, said cleaning device comprising:
- a flexible shaft having a diameter no greater than about two millimeters, said shaft defining a brush end, a second end, and an axis of elongation;
- a brush in the form of the frustum of a cone, said brush being affixed to said shaft near said brush end of said shaft, with the axis of said frustum substantially coincident with said axis of elongation, said brush having a smallest diameter of at least about 2 millimeters, and a largest diameter less than about 5 millimeters; and
- an elastomeric, generally cylindrical swab affixed to said shaft at a location between said brush and said second end of said shaft, said swab having a diameter no smaller than said largest diameter of said brush.

47. A cleaning device according to claim 46, wherein said smallest diameter of said brush is about 2.2 millimeters, and said largest diameter of said brush is about 4.1 millimeters.

48. A cleaning device according to claim 46, wherein said smallest diameter of said brush is about 3.1 millimeters, and said largest diameter of said brush is about 4.1 millimeters.

49. A cleaning device according to claim 46, wherein said smallest diameter of said brush is about 4.1 millimeters, and said largest diameter of said brush is about 4.6 millimeters.

50. A cleaning device for a lumen of a catheter, said cleaning device comprising:
- a flexible shaft having a diameter no greater than about two millimeters, said shaft defining a brush end, a second end, and an axis of elongation;
- a brush in the general form of a right circular cylinder, said brush being affixed to said shaft near said brush end of said shaft, with the axis of said cylinder substantially coincident with said axis of elongation, said brush having a diameter of about 4.1 millimeters; and
- an elastomeric, generally cylindrical swab affixed to said shaft at a location between said brush and said second end of said shaft, said swab having a diameter no smaller than about 4.1 millimeters.

51. A cleaning device according to claim 50, wherein said shaft has a length greater than 100 centimeters.

52. A cleaning device for a lumen of a catheter, said cleaning device comprising:
- a flexible shaft having a diameter no greater than about two millimeters, said shaft defining a brush end, a second end, and an axis of elongation;
- a brush in the general form of a right circular cylinder, said brush being affixed to said shaft near said brush end of said shaft, with the axis of said cylinder substantially coincident with said axis of elongation, said brush having a diameter of about 4.6 millimeters; and
- an elastomeric, generally cylindrical swab affixed to said shaft at a location between said brush and said second end of said shaft, said swab having a diameter no smaller than about 4.6 millimeters.

53. A cleaning device according to claim 52, wherein said shaft has a length greater than 100 centimeters.

54. A method for cleaning a lumen of a catheter, said method comprising the steps of:
- procuring a clean lumen cleaning device comprising a flexible shaft defining a brush end and a second end, said shaft being longer than said lumen, said brush end being fitted with a brush having at least a portion which has a diameter no less than the diameter of said lumen, and no greater than about 10% larger than said diameter of said lumen, said lumen cleaning device further including a swab affixed to said shaft at a location between said brush and said second end of said shaft, said swab having a diameter not less than said diameter of said portion of said brush;
- inserting said brush end of said lumen cleaning device into a first end of said lumen, and pushing said brush end of said lumen cleaning device through said lumen until it exits from the other side of said lumen;
- pulling on said brush end of said lumen cleaning device, to pull the entirety of said lumen cleaning device, including said swab, through said lumen;
- not reintroducing said brush into said lumen, to avoid reintroducing already-removed matter into said lumen; and
- if necessary, repeating said steps of procuring, inserting, pulling, and not reintroducing.

* * * * *